(12) United States Patent
DeWachter (10) Patent No.: US 9,854,764 B2
(45) Date of Patent: Jan. 2, 2018

(54) LOW POPULATION, DROUGHT TOLERANT SOYBEAN VARIETY

(71) Applicant: Richard DeWachter, Otterville (CA)

(72) Inventor: Richard DeWachter, Otterville (CA)

(73) Assignee: 2331535 Ontario LTD, Otterville, Ontario (CA)

( * ) Notice: Subject to any disclaimer, the term of this patent is extended or adjusted under 35 U.S.C. 154(b) by 0 days.

(21) Appl. No.: 14/837,441

(22) Filed: Aug. 27, 2015

(65) Prior Publication Data

US 2016/0057962 A1  Mar. 3, 2016

Related U.S. Application Data

(60) Provisional application No. 62/043,202, filed on Aug. 28, 2014.

(51) Int. Cl.
*A01H 5/10* (2006.01)

(52) U.S. Cl.
CPC ..................... *A01H 5/10* (2013.01)

(58) Field of Classification Search
CPC ....................................................... A01H 5/10
See application file for complete search history.

(56) References Cited

U.S. PATENT DOCUMENTS 8,404,938 B2 * 3/2013 Jury ..................... A01H 5/10
435/415

* cited by examiner

*Primary Examiner* — Russell Kallis
(74) *Attorney, Agent, or Firm* — Schwabe, Williamson & Wyatt (57) ABSTRACT

A low population, drought-tolerant annual soybean (*Glycine max*) variety, in one example known as soybean variety '210197', seed used to produce the soybean, and methods of using the soybean plant and the seed are provided.

31 Claims, 5 Drawing Sheets

LOW POPULATION, DROUGHT TOLERANT SOYBEAN VARIETY

CROSS REFERENCE TO RELATED APPLICATION

This application claims the benefit of U.S. Provisional Patent Application No. 62/043,202, filed Aug. 28, 2014, which is incorporated herein by reference in its entirety.

FIELD

This disclosure relates to a new and distinctive soybean variety, '210197', that is low population, drought tolerant.

BACKGROUND

The soybean (*Glycine max*) is a species of legume native to East Asia and widely grown for its edible bean. Varieties of soybeans are used for many purposes, including being processed into soybean meal and vegetable oil. Traditional fermented food uses of soybeans include soy sauce, fermented bean paste, natto, and tempeh, among others. Examples of non-fermented food uses include soy milk, tofu and tofu skin. Soybeans are thus a globally important crop, providing oil and protein. To maximize crop yield plant population and soil conditions including adequate water supply must be controlled.

SUMMARY

Herein disclosed is an annual soybean (*Glycine max* (L.) Merr.) variety, which is sufficiently low population and drought tolerant to survive extremely low population drought conditions. One example of such a drought tolerant annual soybean is soybean variety '210197'. As used herein, a low population variety is capable of maintaining a significant plant yield, such as at least 45 bushels per acre, including between 45 and 90 bushels per acre, such as 50 to 75 bushels per acre, including 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90 bushels per acre in a low population planting such as approximately 30,000 plants per acre. As used herein, a drought-tolerant annual soybean is capable of tolerating drought conditions which include, but are not limited to, tolerating planting in course, droughty sand with low water holding capacity and tolerating D1 and D2 drought conditions.

A deposit of the new soybean variety '210197' was made with the American Type Culture Collection (ATCC), 10801 University Blvd., Manassas, Va., 20110. The date of deposit is Aug. 3, 2017. The deposit was of 100 packets of seeds, with 25 seeds in each packet. The deposit is intended to meet all of the requirements of 37 C.F.R. §§1.801-1.809. The accession number for those deposited seeds of the new soybean variety '210197' is ATCC Patent Deposit Designation PTA-124296. The deposit will be maintained in the depository for a period of 30 years, or 5 years after the last request, or for the effective life of the patent, whichever is longer, and will be replaced if necessary during that period. In one embodiment, the disclosure provides soybean seed deposited as ATCC Patent Deposit Designation PTA-124296, as well as bulk soybean seed containing such seeds. The variety is also maintained at 2331535 Ontario LTD, 732664 Pick Line, Otterville, Ontario NOJ-1R0.

In one example, the disclosure provides annual soybean plants that include, and in some examples consist of, or consist essentially of, the morphological and physiological characteristics of the annual soybean known as variety '210197', as well as seeds of such plants. In another example, the disclosure provides annual soybean plants having the genotype of '210197'. The disclosure also encompasses annual soybean plants produced by crossing 210197 with other soybean varieties, as well as seeds of such plants. The present disclosure also provides methods of producing soybean seed that include planting seed from '210197' under conditions that result in the germination of the seed, growth of soybean plants and setting of progeny seed, and then harvesting the progeny seed.

The disclosure also provides annual soybean plants produced by exposing '210197' to low population and drought conditions, including exposing plants to D1 or D2 drought severity classification conditions, and selecting those plants which survive such exposures. These methods can be used to identify soybean plants that can tolerate both low population and drought conditions, such as plants that generate significant plant yield, such as 45 bushels per acre in D1 or D2 drought severity classification conditions defined by the U.S. Drought Monitor Classification Scheme (which is hereby incorporated by reference in its entirety as available on Aug. 28, 2014). In particular, D1 drought severity conditions are those of a moderate drought with a Palmer Drought Index of −2.0 to −2.9, a CPC Soil Moisture Model within the 11-20 Percentile, USGS Weekly Streamflow of the 11-20 Percentile, Standardized Precipitation Index of −0.8 to −1.2 and Objective Short and Long-term Drought Indicator Blends of the 11-20 Percentile. D2 drought severity conditions are those of a severe drought with a Palmer Drought Index of −3.0 to −3.9, a CPC Soil Moisture Model within the 6-10 Percentile, USGS Weekly Streamflow of the 5-10 Percentile, Standardized Precipitation Index of −1.3 to −1.5 and Objective Short and Long-term Drought Indicator Blends of the 6-10 Percentile.

The disclosure also provides a tissue culture of regenerable cells of the new soybean variety '210197', as well as plants regenerated therefrom. Such regenerated soybean plants can include or consist of the physiological and morphological characteristics of a plant grown from the seed of the new soybean variety '210197'. Exemplary regenerable cells include but are not limited to those from protoplasts or cells, such as those from embryos, meristematic cells, pollen, leaves, roots, root tips, anther, pistil, flower, seed, cotyledon, hypocotyl, shoot, or stem of the new soybean variety '210197'.

A method is provided for producing a low population planting drought-tolerant soybean plant by crossing a first soybean plant with one or more other soybean plants to produce progeny soybean plants, wherein the first soybean plant is a '210197' variety or a low population, drought-tolerant cross derived from an '210197' variety, and then screening the progeny soybean plants to select a progeny soybean plant that is tolerant to low population planting and drought conditions. Low population drought-tolerant soybean plants produced by this method are also encompassed by the disclosure.

Methods of producing soybean seed from the '210197' soybean plants are provided. In some examples such methods include crossing '210197' with itself or a second soybean plant and harvesting a resulting soybean seed. In some examples, the second soybean plant has one or more desirable traits, which is/are introduced into plants and seeds resulting from such a cross. For example, the second plant can be transgenic, wherein the transgene confers the desirable trait(s). Seeds produced by such methods, including $F_1$ hybrid seeds, as well as soybean plants or parts thereof produced by growing such a seed, are provided. In some examples, the method of crossing includes planting seeds of the new soybean variety '210197', cultivating soybean plants resulting from the seeds until the plants bear flowers, allowing fertilization of the flowers of the plants; and harvesting seeds produced from the plants.

Methods are provided for developing a new soybean plant using the new '210197' variety. For example, the methods can include using '210197' plants or parts thereof as a source of breeding material in plant breeding techniques, such as recurrent selection, mass selection, bulk selection, backcrossing, pedigree breeding, genetic marker-assisted selection and genetic transformation. In some examples, a plant of the new soybean variety '210197' is used as the male or female parent.

The disclosure provides a first generation ($F_1$) hybrid soybean seed produced by crossing a plant of the new soybean variety '210197' to a second soybean plant. In some embodiments, the $F_1$ hybrid soybean plant is grown from the hybrid seed produced by crossing the new soybean variety '210197' to a second soybean plant. In specific examples, provided is a seed of an $F_1$ hybrid plant produced with the new soybean variety '210197' as one parent, the second generation ($F_2$) hybrid soybean plant grown from the seed of the $F_1$ hybrid plant, and the seeds of the $F_2$ hybrid plant.

Methods of producing hybrid soybean seeds are also provided. In one example, the method includes crossing the new soybean variety '210197' to a second, distinct soybean plant which is nonisogenic to the new soybean variety '210197'. In some examples, the method includes cultivating soybean plants grown from seeds of the new soybean variety '210197' and cultivating soybean plants grown from seeds of a second, distinct soybean plant, until the plants bear flowers. A flower on one of the two plants is cross pollinated with the pollen of the other plant, and the seeds resulting from such a cross are harvested.

The disclosure also provides soybean plants and parts thereof produced by any of the methods disclosed herein. Thus, provided herein are plants of soybean variety '210197' that further include a single locus conversion, such as one or more desired traits, for example produced by backcrossing or genetic transformation. In some embodiments, the soybean plants produced by the disclosed methods includes at least two, at least three, at least four, at least five, or at least 10 of the traits of the new soybean variety '210197' as described herein. In some embodiments, the soybean plants produced by the disclosed methods include at least two, at least three, at least four, at least five, or at least 10 of the traits of the new soybean variety '210197' such as glyphosate tolerance, as described herein.

Methods of producing a commodity plant product are provided. In some examples the method includes obtaining or supplying a plant of the new soybean variety '210197', or a part thereof, and producing the commodity plant product therefrom. In some examples the method includes growing and harvesting the plant, or a part thereof. Exemplary commodity plant products include but are not limited to a protein concentrate, a protein isolate, soybean hulls, meal, flour or oil.

The foregoing and other features and advantages of the disclosure will become more apparent from the following detailed description, which proceeds with reference to the accompanying figures.

DETAILED DESCRIPTION

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants and reference to "the seed" includes reference to one or more seeds and equivalents thereof known to those skilled in the art, and so forth. The term "or" refers to a single element of stated alternative elements or a combination of two or more elements, unless the context clearly indicates otherwise. For example, the phrase "A or B" refers to A, B, or a combination of both A and B.

Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Backcross: The mating of a hybrid to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Cell. Cell as used herein includes a plant cell, whether isolated, in tissue culture or incorporated in a plant or plant part.

Cross. Synonymous with hybridize or crossbreed. Includes the mating of genetically different individual plants, such as the mating of two parent plants.

Cross-pollination: Fertilization by the union of two gametes from different plants.

$F_1$ hybrid: The first generation progeny of the cross of two nonisogenic plants.

Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

Lodging: The visual rating of the uprightness of the plants. The score is based on the average of the plants in a plot with a score of 1 to 5, with a score of 1 indicating all plants are erect, and a score of 5 where over about 80% of the plants in a plot are prostrate.

Maturity date: The evaluation of plants considered as mature when about 95% of the pods have reached their mature color.

Plant: Includes reference to an immature or mature whole plant, including a plant from which seed, roots or leaves have been removed. Seed or embryo that will produce the plant is also considered to be the plant.

Plant height. Plant height is taken from the top of the soil to the tip of the plant, and is typically measured in centimeters or inches.

Plant parts. Includes protoplasts, leaves, stems, roots, root tips, anthers, pistils, seed, embryo, pollen, ovules, cotyledon, hypocotyl, flower, shoot, tissue, petiole, cells, calli, pods, meristematic cells and the like. Includes plant cells of a tissue culture from which soybean plants can be regenerated.

Progeny. Offspring; descendants.

Regeneration. The development of a plant from tissue culture. The cells may, or may, not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Relative maturity: Refers to the maturity grouping designated by the soybean industry over a given growing area. This figure is generally divided into tenths of a relative maturity group. Within narrow comparisons, the difference of a tenth of a relative maturity group equates very roughly to a day difference in maturity at harvest.

Seed. The part of a flowering plant that typically contains the embryo with its protective coat and stored food and that can develop into a new plant under the proper conditions; fertilized and mature ovule.

Seed quality: The visual rating of the completeness of the seed. The score is based on the completeness of the seed coat and overall soundness of the seed. Scores range from 1 to 5, with a score of 1 indicating good quality seed and a score of 5 indicating the seeds are of poor quality.

Seed yield: The yield in bushels/acre (bu/a) and is the actual yield of the grain at harvest.

Self-pollination: The transfer of pollen from the anther to the stigma of the same plant.

Single locus converted (conversion) plant: Plants developed by backcrossing and/or by genetic transformation, wherein essentially all of the desired morphological and physiological characteristics of a soybean variety are recovered in addition to the characteristics of the single locus transferred into the variety via the backcrossing technique.

Tissue culture: A composition that includes isolated cells of the same or a different type or a collection of such cells organized into parts of a plant.

Transformation. The introduction of new genetic material (e.g., exogenous transgenes) into plant cells. Exemplary mechanisms that are to transfer DNA into plant cells include (but not limited to) electroporation, microprojectile bombardment, Agrobacterium-mediated transformation and direct DNA uptake by protoplasts.

Transgene. A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a soybean plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

EXAMPLES

The following examples are provided to better describe the present disclosure and to guide those of ordinary skill in the art in the practice of the present disclosure.

Example 1

Origin and Breeding History

Soybean variety '210197' began as a cross between the sister lines 0301 and 0306 in 2001. 0301 and 0306 were derived from a cross of Crusher and Legacy in 1999. Bulk and modified single plant descent methods were used in developing the variety. F1 seed from promising progeny were collected and planted in 2002. F2 seed from the best 5 plants was collected, pooled and planted in 2003. Single plant selection was done from 2003 through to the final selection in 2007. Seed from this final selection was used to increase seed supply from 2008 to 2012. Every year the best 3 to 5 plants were selected for breeding. All field testing was done in Otterville, Ontario. Selection criteria included plant phenotype, agronomic performance and seed yield.

Plots consisted of 3 rows with a row length of 60 meters and a row spacing of 40 cm. There were 4 replicates.

Soybean variety '210197' was been found to be uniform and stable in plant morphology. Exceptions were an occasional plant with tawny pubescence, less than 1 per 1000. It has been uniform and stable for the last 5 generations.

Example 2

Distinction Statement for '210197'

The variety '210197' is similar to the check varieties DH410SCN, Thames, and S20-G7 in that it has approximately the same height and plant shape when planted at conventional populations. All four evaluated varieties were also non-genetically modified organisms (GMO). Where '210197' was distinct from the check varieties DH410SCN, Thames, and S20-G7, is that it produced more and larger branches with higher pod counts per node. This enabled it to compensate for extremely low populations with no loss of yield.

Example 3

Seed Deposit

Seeds of the soybean variety referred to herein as '210197', will be deposited with the ATCC (Manassas, Va.). The variety is also maintained at 2331535 Ontario LTD, 732664 Pick Line, Otterville, Ontario NOJ-1R0.

Example 4

Morphological Characteristics

The morphological characteristics of soybean variety '210197' are shown in Tables 1 below. Soybean plants were established, arranged and maintained as detailed in Example 1. At 133 days maturity, plant height for soybean variety '210197' was 63 cm in the first year at location 1 and 70 cm height in the second year at location 2 (compared to most similar variety Thames which was 46 cm and 63 cm at day 128 of maturity). Variations on these measurements may be observed for plants of differing ages, grown in other locations, or under different prevailing weather conditions.

TABLE 1

Plant Morphological Measurements in Soybean variety '210197'

| Morphology | |
| --- | --- |
| Seed Shape | Spherical-Flattened (L/W ratios >1.2; L/T ratios ≤1.2) |
| Seed Coat Color | Yellow |
| Seed Coat Luster | Dull |
| Seed Size | 16.3 grams/100 seeds |
| Hilum Color | Brown |
| Cotyledon Color | Green |
| Hypocotyl Color | Green with Bronze |
| Leaf Color | Medium Green |
| Flower Color | Purple |
| Pod Color | Brown |
| Pubescence Color | Brown (Tawny) |
| Plant Type | Bushy |
| Plant Height | Tall |
| Plant Growth Type | Indeterminate |
| Plant Habit | Erect to semi-erect |
| Maturity Group | II |
| Maturity Subgroup | 1 |
| Herbicide Reaction | Susceptible to Glyphosate |

Example 5

Low Population, Drought Tolerance

This example provides methods and results of field trials in which the low population, drought tolerant characteristics of soybean variety '210197' were examined and compared with the most similar variety Thames as well as other similar varieties DH410SCN and/or S20-G7.

Field #1 Description

This field was planted in May and was harvested in early November. All plots consisted of 3 rows 15' apart and approximately 200 ft. long. The final length of each row was measured at harvest. The South end of the field is a sandy loam with average water capacity. The North end of the field is sand with poor water capacity. In all charts, '210197' is designated as variety C and Thames as variety D. For a complete list of what each letter represents please refer to Trials Map, Letter definitions and Map/Chart provided below.

Letter Definitions and Map/Chart

A—DH410
B—520-G7
C—'210197'
D—Thames
H—High Population
M—Medium Population
L1—Low population First Trial
L2—Low population Second Trial
1—1st Replication, starts at South End of Field
2—2nd Replication, starts North of 1st replication
3—3rd Replication, starts North of 2nd replication
4—4th Replication, starts North of 3rd replication
UC Plots were hand-thinned to 8000 plants/acre '210197' Trials Map

| | | | East | | | | |
| --- | --- | --- | --- | --- | --- | --- | --- |
| HC4 | Lane | HB3 | Lane | HA2 | Lane | HD1 | Lane |
| HB4 | | HA3 | | HD2 | | HC1 | |
| HA4 | | HD3 | | HC2 | | HB1 | |
| HD4 | | HC3 | | HB2 | | HA1 | |
| MC4 | | MB3 | | MA2 | | MD1 | |
| MB4 | | MA3 | | MD2 | | MC1 | |
| MA4 | | MD3 | | MC2 | | MB1 | |
| MD4 | | MC3 | | MB2 | | MA1 | |
| North L1C4 | | L1B3 | | L1A2 | | L1D1 | South |
| L1B4 | | L1A3 | | L1D2 | | L1C1 | |
| L1A4 | | L1D3 | | L1C2 | | L1B1 | |
| L1D4 | | L1C3 | | L1B2 | | L1A1 | |
| L2C4 | | L2B3 | | L2A2 | | L2D1 | |
| L2B4 | | L2A3 | | L2D2 | | L2C1 | |
| L2A4 | | L2D3 | | L2C2 | | L2B1 | |
| L2D4 | | L2C3 | | L2B2 | | L2A1 | |
| UC4 | | UC3 | | UC2 | | UC1 | |
| | | | West | | | | |

In the South end of the field (Plot 1), 21097(C) ws consistent in yield across the plot, whereas Thames (D) and other similar varieties lost significant yield when the population dropped to approximately 30,000 plants per acre. Plant height results are shown in Tables 1.

TABLE 1

Plant Height (cm)

| | | Average of 10 subsample measurements | Replicate Average | Replicate StdDev |
|---|---|---|---|---|
| High Population South | A | 86 | 69.5 | 23.3 |
| High Population North | A | 53 | | |
| High Population South | B | 95.5 | 78.05 | 24.7 |
| High Population North | B | 60.6 | | |
| High Population South | C | 115.6 | 89.4 | 37.1 |
| High Population North | C | 63.2 | | |
| High Population South | D | 83.1 | 72.45 | 15.1 |
| High Population North | D | 61.8 | | |
| Medium Population South | A | 84.2 | 68.9 | 21.6 |
| Medium Population North | A | 53.6 | | |
| Medium Population South | B | 91.1 | 72.65 | 26.1 |
| Medium Population North | B | 54.2 | | |
| Medium Population South | C | 98.5 | 87.6 | 15.4 |
| Medium Population North | C | 76.7 | | |
| Medium Population South | D | 90.1 | 67.95 | 31.3 |
| Medium Population North | D | 45.8 | | |
| Low 1 Population South | A | 68.8 | 57 | 16.7 |
| Low 1 Population North | A | 45.2 | | |
| Low 1 Population South | B | 63.3 | 54.5 | 12.4 |
| Low 1 Population North | B | 45.7 | | |
| Low 1 Population South | C | 69.9 | 66.5 | 4.8 |
| Low 1 Population North | C | 63.1 | | |
| Low 1 Population South | D | 67.4 | 53.7 | 19.4 |
| Low 1 Population North | D | 40 | | |
| Low 2 Population South | A | 75.2 | 61.6 | 19.2 |
| Low 2 Population North | A | 48 | | |
| Low 2 Population South | B | 69.9 | 64.9 | 7.1 |
| Low 2 Population North | B | 59.9 | | |
| Low 2 Population South | C | 104.2 | 88.65 | 22.0 |
| Low 2 Population North | C | 73.1 | | |
| Low 2 Population South | D | 77.9 | 63.4 | 20.5 |
| Low 2 Population North | D | 48.9 | | |

The replicate average is the average of the height measurements from the south and north plots.

Figure 1:
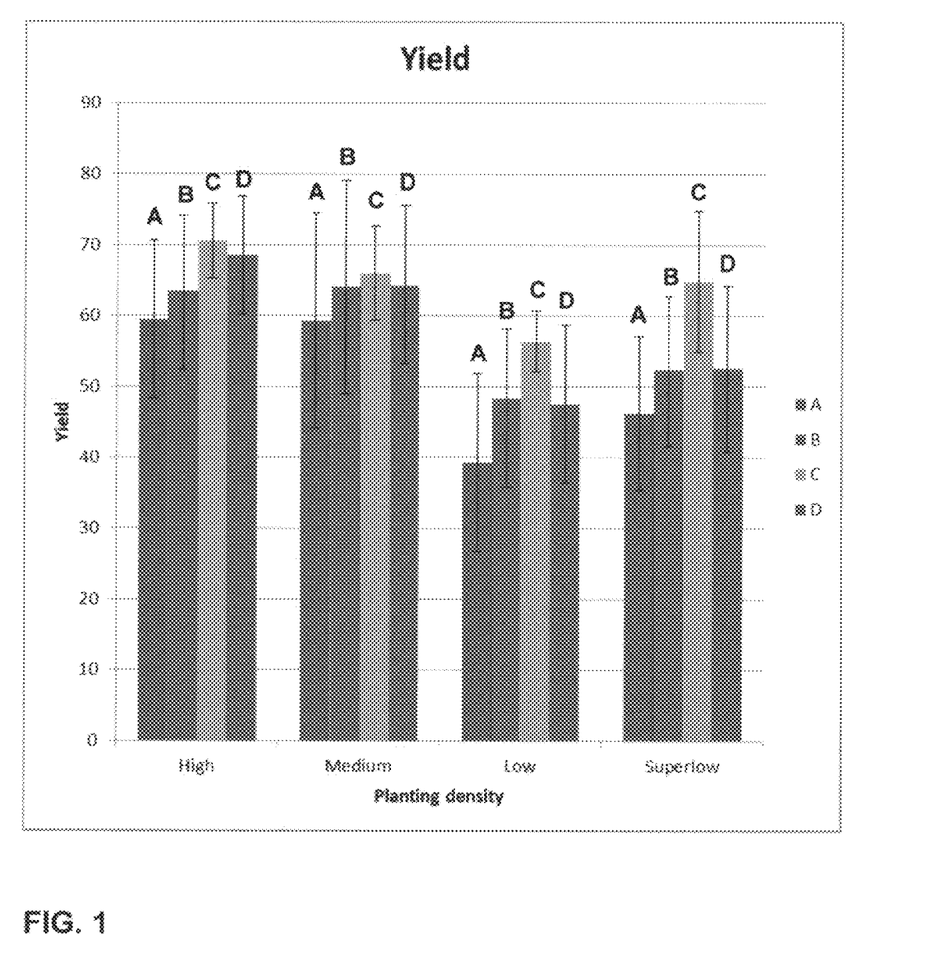
FIG. 1 is a graph illustrating plant population under various plant population planting conditions (high, medium, low and superlow).

Plant yield in bu/acre are shown in Tables 2 and 3 and FIG. 1.

TABLE 2

| Block | | | | Average of 10 subsample measurements | Replicate Average | Replicate StdDev |
|---|---|---|---|---|---|---|
| High Population | 1 | North | A | 45.9 | 59.475 | 11.2 |
| High Population | 2 | | A | 59.1 | | |
| High Population | 3 | | A | 59.6 | | |
| High Population | 4 | South | A | 73.3 | | |
| High Population | 1 | North | B | 49.7 | 63.575 | 10.5 |
| High Population | 2 | | B | 61.1 | | |
| High Population | 3 | | B | 72.1 | | |
| High Population | 4 | South | B | 71.4 | | |
| High Population | 1 | North | C | 63.3 | 70.575 | 5.3 |
| High Population | 2 | | C | 70.1 | | |
| High Population | 3 | | C | 74.1 | | |
| High Population | 4 | South | C | 74.8 | | |
| High Population | 1 | North | D | 57.7 | 68.475 | 8.4 |
| High Population | 2 | | D | 68.2 | | |
| High Population | 3 | | D | 78.1 | | |
| High Population | 4 | South | D | 69.9 | | |
| Medium Population | 1 | North | A | 46.5 | 59.275 | 15.2 |
| Medium Population | 2 | | A | 46.2 | | |
| Medium Population | 3 | | A | 68.8 | | |
| Medium Population | 4 | South | A | 75.6 | | |
| Medium Population | 1 | North | B | 43.8 | 64.175 | 15.0 |
| Medium Population | 2 | | B | 62.9 | | |
| Medium Population | 3 | | B | 78.3 | | |
| Medium Population | 4 | South | B | 71.7 | | |
| Medium Population | 1 | North | C | 60.4 | 66.025 | 6.6 |
| Medium Population | 2 | | C | 60.9 | | |
| Medium Population | 3 | | C | 68.5 | | |
| Medium Population | 4 | South | C | 74.3 | | |
| Medium Population | 1 | North | D | 51.4 | 64.325 | 11.2 |
| Medium Population | 2 | | D | 58.9 | | |
| Medium Population | 3 | | D | 75.6 | | |
| Medium Population | 4 | South | D | 71.4 | | |
| Low 1 Population | 1 | North | A | 33.7 | 39.3 | 12.6 |
| Low 1 Population | 2 | | A | 25.4 | | |
| Low 1 Population | 3 | | A | 54.5 | | |
| Low 1 Population | 4 | South | A | 43.6 | | |
| Low 1 Population | 1 | North | B | 34 | 48.4 | 9.8 |
| Low 1 Population | 2 | | B | 51.8 | | |
| Low 1 Population | 3 | | B | 51.7 | | |
| Low 1 Population | 4 | South | B | 56.1 | | |
| Low 1 Population | 1 | North | C | 50.6 | 56.375 | 4.3 |
| Low 1 Population | 2 | | C | 59.6 | | |
| Low 1 Population | 3 | | C | 59.7 | | |
| Low 1 Population | 4 | South | C | 55.6 | | |
| Low 1 Population | 1 | North | D | 33.7 | 47.6 | 11.2 |
| Low 1 Population | 2 | | D | 43.7 | | |
| Low 1 Population | 3 | | D | 58.4 | | |
| Low 1 Population | 4 | South | D | 54.6 | | |
| Low 2 Population | 1 | North | A | 33.6 | 46.225 | 10.8 |
| Low 2 Population | 2 | | A | 44 | | |
| Low 2 Population | 3 | | A | 59.9 | | |
| Low 2 Population | 4 | South | A | 47.4 | | |

TABLE 2-continued

| Block | | | | Average of 10 subsample measurements | Replicate Average | Replicate StdDev |
|---|---|---|---|---|---|---|
| Low 2 Population | 1 | North | B | 38.2 | 52.4 | 10.3 |
| Low 2 Population | 2 | | B | 52.9 | | |
| Low 2 Population | 3 | | B | 62.8 | | |
| Low 2 Population | 4 | South | B | 55.7 | | |
| Low 2 Population | 1 | North | C | 54.4 | 64.825 | 9.9 |
| Low 2 Population | 2 | | C | 59.1 | | |
| Low 2 Population | 3 | | C | 69.7 | | |
| Low 2 Population | 4 | South | C | 76.1 | | |
| Low 2 Population | 1 | North | D | 36.5 | 52.575 | 11.7 |
| Low 2 Population | 2 | | D | 51.3 | | |
| Low 2 Population | 3 | | D | 61.8 | | |
| Low 2 Population | 4 | South | D | 60.7 | | |

TABLE 3

| | Yield (ave of the 4 replicates) | | | | Yield (StdDev) | | | |
|---|---|---|---|---|---|---|---|---|
| | High | Medium | Low 1 | Low 2 | High | Medium | Low 1 | Low 2 |
| A | 59.475 | 59.275 | 39.3 | 46.225 | 11.1888 | 15.18099 | 12.57113 | 10.84324 |
| B | 63.575 | 64.175 | 48.4 | 52.4 | 10.52849 | 14.97673 | 9.816653 | 10.34311 |
| C | 70.575 | 66.025 | 56.375 | 64.825 | 5.27344 | 6.645989 | 4.297577 | 9.871634 |
| D | 68.475 | 64.325 | 47.6 | 52.575 | 8.383466 | 11.16046 | 11.16632 | 11.7068 |

Figure 2:
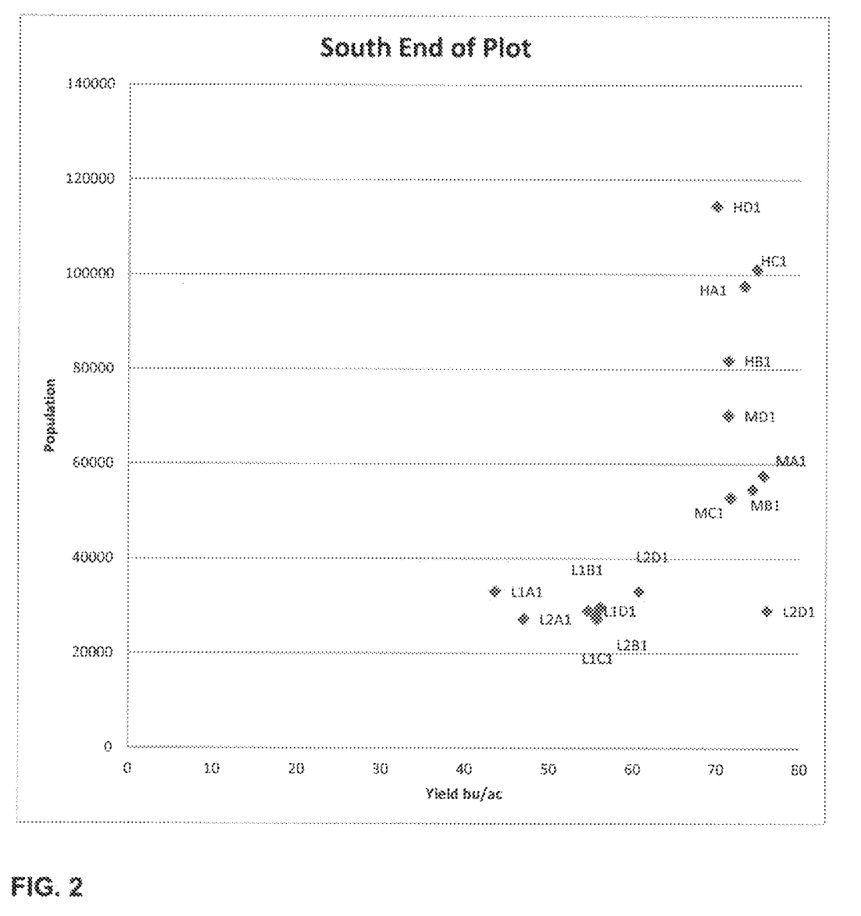
FIG. 2 is a graph of a South end of the field (Plot 1), illustrating soybean variety 21097 was consistent in yield across the plot, whereas similar Thames and other similar varieties lost significant yield when the population dropped to approximately 30,000 plants per acre.

Further the overall average of the yield bushel per acre at a particular population is shown in the Table 4 and FIG. 2.

TABLE 4

| Yield bu/ac | Population | |
|---|---|---|
| 43.6 | 33117 | L1A1 |
| 47 | 27307 | L2A1 |
| 54.6 | 29050 | L1D1 |
| 55.6 | 27888 | L1C1 |
| 56.1 | 29631 | L1B1 |
| 55.7 | 27307 | L2B1 |
| 60.7 | 33117 | L2D1 |
| 76.1 | 29050 | L2C1 |
| 71.7 | 52871 | MB1 |
| 74.32 | 54614 | MC1 |
| 75.6 | 57519 | MA1 |
| 71.4 | 70301 | MD1 |
| 71.4 | 81921 | HB1 |
| 73.3 | 97608 | HA1 |
| 74.8 | 101094 | HC1 |
| 69.9 | 114457 | HD1 |

Figure 3:
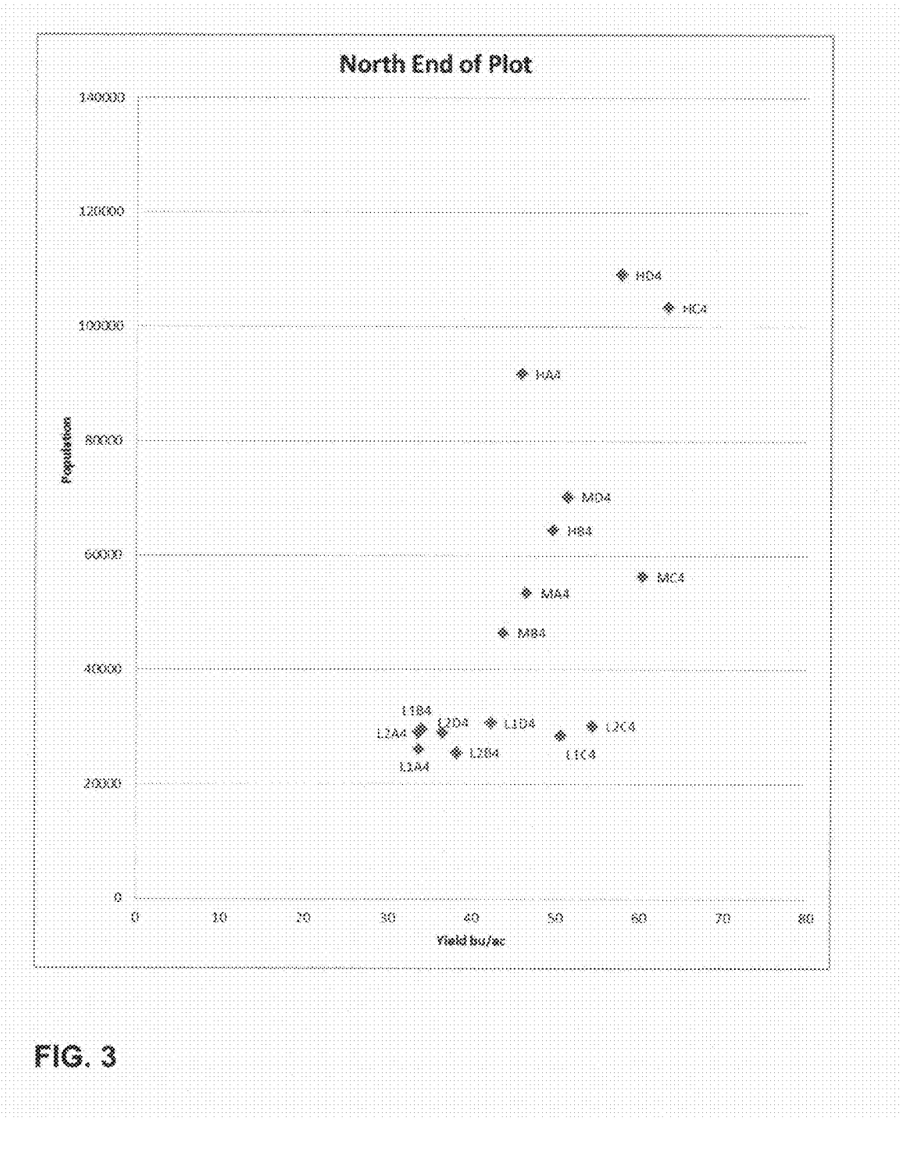
FIG. 3 is a graph of a North end of the field (Plot 1), illustrating soybean variety 21097 was consistent in yield across the plot, whereas similar Thames and other similar varieties lost significant yield when the population dropped to approximately 30,000 plants per acre.

In the North end of the field (Plot 4), '210197' (C) again, maintained the best yields showing resilience to both extremely low population and drought stress when compared to Thames and other similar varieties (Table 5 and FIG. 3).

TABLE 5

| Yield bu/ac | Population | |
|---|---|---|
| 33.6 | 29050 | L2A4 |
| 34 | 29631 | L1B4 |
| 36.5 | 29050 | L2D4 |
| 33.7 | 26145 | L1A4 |
| 38.2 | 25564 | L2B4 |
| 42.3 | 30793 | L1D4 |
| 50.6 | 28469 | L1C4 |
| 54.4 | 30212 | L2C4 |
| 43.8 | 46480 | MB4 |
| 46.5 | 53452 | MA4 |
| 60.35 | 56357 | MC4 |
| 49.7 | 64491 | HB4 |
| 51.4 | 70301 | MD4 |
| 45.9 | 91798 | HA4 |
| 63.3 | 103418 | HC4 |
| 57.7 | 109228 | HD4 |

Field #2 Description

This field was planted in May and was harvested in November. It was planted in 30' rows and had thinned to approximately 16,000 plants per acre based on seed drop. Plot 4 and 5 are loamy sand with poor water holding capacity. Plot size was 0.12 acres for both. Final population was 15,660 for Plot 4 (Thames), with a final yield of 24.47 bu/acre, while Plot 5 ('210197' (C)) had a final population of 13,050 with a yield of 39.32 bu/acre. Plot 7 and 8 were coarse sand with very poor water holding capacity. Plot size was also 0.12 acres in size for both plants. Final population was 14,355 for Plot 7 ('210197' (C)) with a final yield of 32.49 bu/acre, while Plot 8 (Thames) had a final population of 17,400 and a yield of 14.41 bu/acre.

Figure 4:
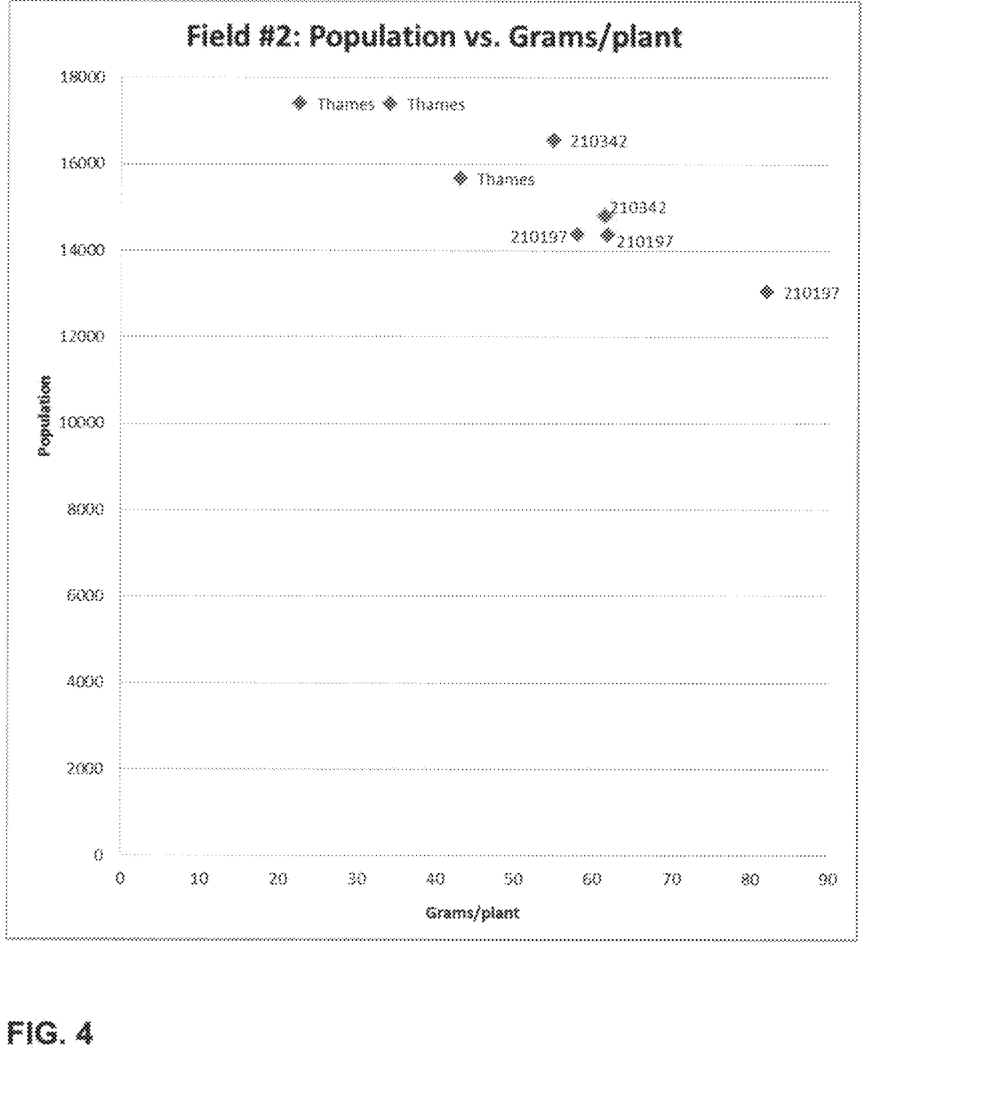
FIG. 4 is a graph illustrating plant population versus grams per plant under Field #2 conditions.
Figure 5:
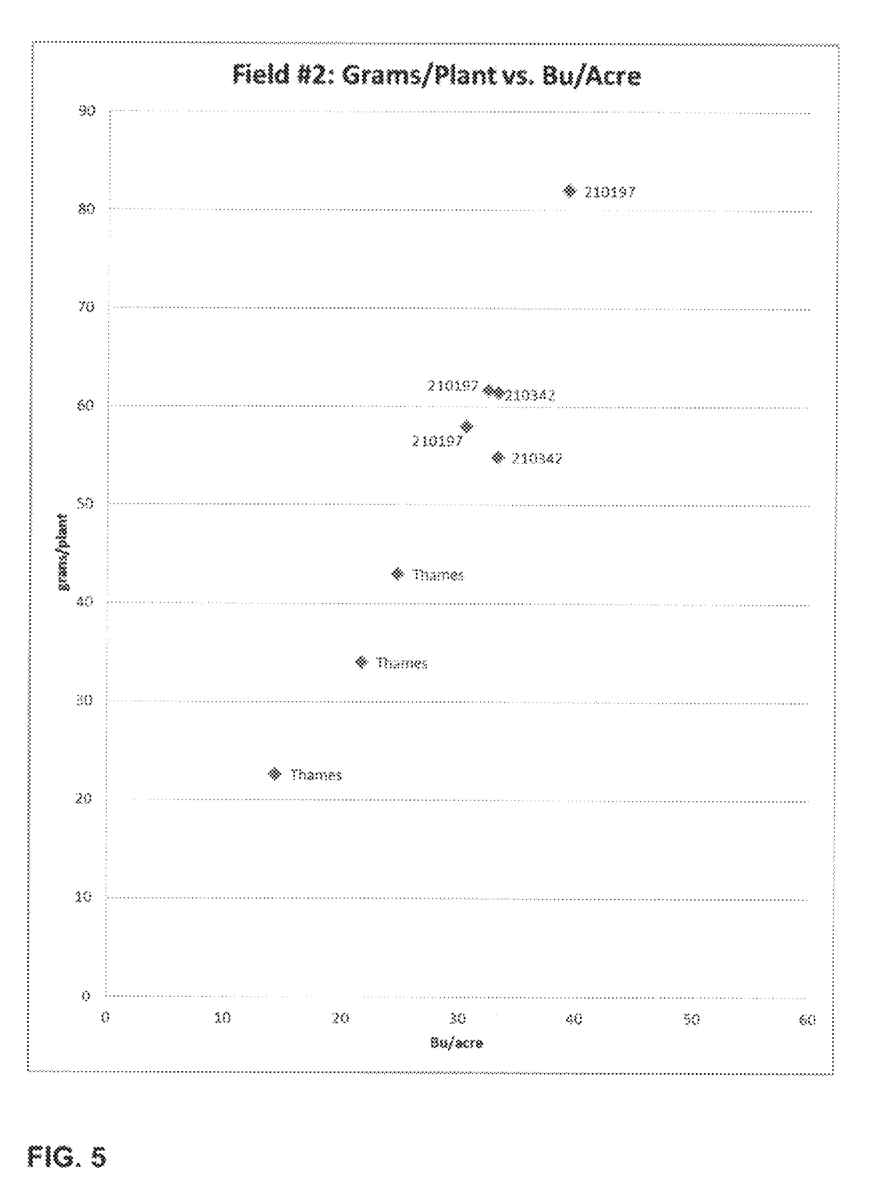
FIG. 5 is a graph illustrating bushels per acre and grams per plant under Field #2 conditions.

When calculating yield versus population in Plot 4 and 5, Plot 4 (Thames) had an average of 43 grams of seed per plant versus Plot 5 ('210197' (C)) with an average of 82 grams of seed per plant. Plot 7 ('210197' (C)) yielded 61.7 grams of seed per plant versus Plot 8 (Thames) at 22.6 grams of seed per plant. These results are shown in Table 6 and FIG. 4. Table 7 and FIG. 5 provide the bushels per acre and grams per plant for 8 different plots.

TABLE 6

| Grams/Plant | Population | |
|---|---|---|
| 61.43 | 14810 | Plot 1: 210342 |
| 54.87 | 16552 | Plot 2: 210342 |
| 34 | 17400 | Plot 3: Thames |
| 43 | 15660 | Plot 4: Thames |
| 82 | 13050 | Plot 5: '210197' |
| 58 | 14374 | Plot 6: '210197' |
| 61.7 | 14355 | Plot 7: '210197' |
| 22.59 | 17400 | Plot 8: Thames |

TABLE 7

| Bu/Acre | Grams/Plant | |
|---|---|---|
| 33.36 | 61.43 | Plot 1: 210342 |
| 33.3 | 54.87 | Plot 2: 210342 |
| 21.69 | 34 | Plot 3: Thames |
| 24.74 | 43 | Plot 4: Thames |
| 39.32 | 82 | Plot 5: '210197' |
| 30.6 | 58 | Plot 6: '210197' |
| 32.49 | 61.7 | Plot 7: '210197' |
| 14.41 | 22.59 | Plot 8: Thames |

In a separate study plots were thinned to approximately 8000 plant per acre and the results shown below in Table 8.

TABLE 8

'210197' Hand Thinned Plots

UC1- 43.7 bu/ac. 158 grams/plant. 120 plants harvested
UC2- 34.8 bu/ac 133 grams/plant. 131 plants harvested
UC3- 29.8 bu/ac. 107 grams/plant. 140 plants harvested
UC4- 35.3 bu/ac. 106 grams/plant 165 plants harvested In conclusion, '210197' was significantly more able to maintain yield in low population and drought conditions. These studies illustrate that '210197' is capable of thriving in low population and drought conditions.

Example 6

Production of Low Population, Drought-Tolerant Soybean Plants

Soybean variety '210197' plants can be grown under normal conditions for growing similar soybean varieties, and bulk seed for large-scale planting can be obtained by methods known in certified seed production. For example, bulk seed can be produced by planting '210197' variety seeds obtained from ATCC (Accession Number PTA-5781) or 2331535 Ontario LTD, 732664 Pick Line, Otterville, Ontario N0J-1R0, allowing the mature plants to produce seed by cross-pollination with each other and then collecting the seed. Standard precautions should be taken to prevent cross-pollination from other soybeans, such as growing the variety in an isolated plot of sterilized soil, removing adjacent vegetation, etc.

To confirm maintenance of the low population, drought-tolerance characteristic, plants would be subjected to a low population planting (e.g., 30,000 plants per acre and would be grown in fields that have a course sandy type soil with a history of poor water holding capacity. Plants that generated 50 grams of seed per plant in the conditions would be identified as low population, drought-tolerate plants.

Example 7

Exemplary Uses of the Low Population, Drought Tolerant Soybean Variety '210197'

The annual soybean variety '210197' can be used in the same way as other annual soybean varieties. However, the tolerance to low population and drought affords '210197' variety particular advantages over other varieties. For example, with current commercially available varieties of non-GMO soybean varieties, the preparation of a soybean crop that is to be made by seeding requires extensive plantings and preparation of the soil including water at a sufficient level. With soybean variety '210197', such preparation can be avoided since such variety can withstand reduced population and water/soil conditions. Variety '210197' would need no irrigation or less irrigation than current varieties. Thus, soybean variety '210197' is especially marketable and therefore useful.

Example 8

Introducing Traits of '210197' into Other Soybean Varieties

The morphological and physiological characteristics of the soybean variety '210197', including the low population, drought tolerance trait, can be introduced into other soybean varieties by conventional breeding techniques. For example, the '210197' variety can be grown in pollination proximity to another variety of soybean, allowing cross-pollination to occur between the '210197' variety and the other variety, and then harvesting the hybrid seeds. Plants grown from these hybrid seeds can then be tested for the maintenance of the molecular characteristics described above for the '210197' variety, or the plants can simply be observed to see if they display the same characteristics described in the above tables.

For example, plants grown from these hybrid seeds can be tested for low population, drought tolerance by application to low population, drought conditions, by growing in fields that are prone to drought or by growing in a controlled environment such as a greenhouse or growth chamber. In this way, the low population, drought tolerance characteristics can be combined with other desirable plant characteristics. Thus, the provision of '210197' enables the production of progeny plants of '210197' having the low population, drought tolerance characteristics. "Progeny plants" of '210197' are any plants that are the offspring of a cross between '210197' and any other plant or plants. Progeny plants also include successive generations of the offspring, for example those selected for low population, drought tolerance using the methods described herein. First-generation progeny plants may retain the low population, drought tolerance characteristic of the '210197' parent. However, if a first-generation progeny plant does not retain the desired level of low population, drought tolerance observed with '210197', subsequent generations of offspring can be recycled for drought tolerance which have at least the same resistance characteristics of '210197' described herein, such capable of tolerating plantings at 30,000 plants per acre and generating 45 bushels per acre. In one example, subsequent generations of offspring can have a low population, drought tolerance that exceeds that of '210197', for example capable of tolerating plantings at 25,000 plants per acre and a D2 drought.

In addition, soybean variety '210197' can be used as transformation targets for the production of transgenic soybeans. In certain examples, the present disclosure contemplates the transformation of cells derived from the '210197' variety with at least one transgene. Transgenes that can be used, include, but are not limited to, transgenes that confer resistance to herbicides, insect, disease (viral, bacterial, fungal, nematode) or standability, prolificacy, salt damage resistance, and quality. Examples of such genes and methods of transforming plants are described in U.S. Pat. No. 6,025,545 to Lundquist et al. and Jain and Jain (*Indian J. Exp. Biol.* 38:6-17, 2000) herein incorporated by reference.

Having illustrated and described the principles of the disclosure in multiple embodiments and examples, it should be apparent to those skilled in the art that the disclosure can be modified in arrangement and detail without departing from such principles. The invention, therefore, encompasses all modifications coming within the spirit and scope of the following claims

I claim:

1. A soybean plant of a soybean variety '210197', representative sample seed of the variety is deposited under American Type Culture Collection (ATCC) Patent Deposit Designation PTA-124296.

2. Seed of the soybean plant of claim 1.

3. A seed mixture, comprising the seed of claim 2.

4. A vegetative sprig or clone of the soybean plant of claim 1.

5. The soybean plant of claim 1, further comprising at least one transgene.

6. The soybean plant of claim 5, wherein the at least one transgene confers upon the soybean plant resistance to a bacterial disease, viral disease, fungal disease, nematode, or insect.

7. The soybean plant of claim 5, wherein the at least one transgene confers upon the soybean plant drought tolerance or salt tolerance.

8. Seed resulting from crossing the soybean plant of claim 1 with a second soybean plant.

9. A soybean plant grown from the seed of claim 8.

10. A method of producing soybean seed, comprising
planting the seed of claim 2 under conditions that result in the germination of the seed, growth of soybean plants and setting of progeny seed; and
harvesting the progeny seed.

11. Soybean seed produced by the method of claim 10.

12. A mixture of soybean seed comprising the soybean seed of claim 11.

13. A method of producing a low population, drought-tolerant soybean plant, comprising:
crossing a first soybean plant with at least one other soybean plant to produce progeny soybean plants, wherein the first soybean plant is the soybean plant of claim 1;
screening the progeny soybean plants to select a progeny soybean plant that is tolerant to low population, drought conditions.

14. A low population, drought-tolerant soybean plant produced by the method of claim 13.

15. A vegetative sprig or clone of the low population, drought-tolerant soybean plant of claim 14.

16. The low population, drought-tolerant soybean plant of claim 14, further comprising at least one transgene.

17. The low population, drought-tolerant soybean plant of claim 16, wherein the at least one transgene confers upon the soybean plant resistance to a bacterial disease, viral disease, fungal disease, nematode, or insect.

18. The low population, drought-tolerant soybean plant of claim 14, wherein the soybean plant is tolerant to plantings of 30,000 plants per acre.

19. The low population, drought-tolerant soybean plant of claim 14, wherein the soybean plant generates such as 45 bushels per acre in a low population planting of 30,000 plants per acre.

20. The low population, drought-tolerant soybean plant of claim 14, wherein the soybean plant generates 50 grams of seed per plant in a low population planting of 30,000 plants per acre.

21. A seed of soybean variety '210197', representative sample seed of the variety is deposited under American Type Culture Collection (ATCC) Patent Deposit Designation PTA-124296.

22. A method of producing soybean seed, comprising
planting the soybean seed of claim 21 under conditions that result in the germination of the soybean seed, growth of soybean plants and setting of progeny seed; and
harvesting the progeny seed.

23. Soybean seed produced by the method of claim 22.

24. A mixture of soybean seed comprising the soybean seed of claim 23.

25. A soybean plant germinated from the seed of claim 23.

26. A soybean plant produced from the soybean plant of claim 25 by transformation with a transgene that confers upon the soybean plant resistance to a bacterial disease, viral disease, fungal disease, nematode, or insect.

27. A method of producing a low population, drought-tolerant soybean plant, comprising:
exposing the soybean plant of claim 1 to a population of <30,000 plants per acre and D2 drought conditions, thereby generating exposed soybean plants;
selecting exposed soybean plants that are tolerant to the low population, drought conditions.

28. The method of claim 27, wherein the soybean plant of claim 1 is planted at 30,000 plants per acre.

29. The method of claim 27, wherein the soybean plant of claim 1 is planted at 20,000 plants per acre.

30. A method of producing a commodity plant product comprising:
obtaining the soybean plant of claim 1 or a part thereof; and
producing the commodity plant product therefrom.

31. The method of claim 30, wherein the commodity plant product is protein concentrate, protein isolate, soybean hulls, meal, flour or oil.

* * * * *